(12) United States Patent
Tedoldi

(10) Patent No.: US 7,522,954 B2
(45) Date of Patent: Apr. 21, 2009

(54) DEVICE FOR THE TRANSCUTANEOUS ADMINISTRATION OF SUBSTANCES BY MEANS OF IONTOPHORESIS

(75) Inventor: Ezio Tedoldi, Rubiera (IT)

(73) Assignee: M & T S.r.l., Rimini (IT)

( * ) Notice: Subject to any disclaimer, the term of this patent is extended or adjusted under 35 U.S.C. 154(b) by 1030 days.

(21) Appl. No.: 10/858,458

(22) Filed: Jun. 1, 2004

(65) Prior Publication Data

US 2005/0267399 A1 Dec. 1, 2005

(51) Int. Cl.
*A61N 1/30* (2006.01)

(52) U.S. Cl. ...................................... 604/20

(58) Field of Classification Search ............ 604/20, 604/22, 890.1, 891.1, 892.1
See application file for complete search history.

(56) References Cited

U.S. PATENT DOCUMENTS 5,983,131 A * 11/1999 Weaver et al. ............... 604/20

FOREIGN PATENT DOCUMENTS

| GB | 2 372 705 A | 9/2002 |
|---|---|---|
| WO | WO 00/10640 | 3/2000 |
| WO | WO 00/56400 | 9/2000 |
| WO | WO 02/09807 A1 | 2/2002 |

* cited by examiner

*Primary Examiner*—Nicholas D Lucchesi
*Assistant Examiner*—Christopher D Koharski
(74) *Attorney, Agent, or Firm*—Pearne & Gordon LLP

(57) ABSTRACT

A device for the transcutaneous administration of substances by means of iontophoresis comprises an operative head (1) provided with an inlet (2) for a fluid transporting substances to be administered, with a dispenser (3) of the fluid which has a part (30) in contact with the skin, with an electrode (4) positioned on a path of the fluid from the inlet (2) to the dispenser (3). The dispenser (3) is made of an electrically conducting material and it is in electrical contact with the electrode (4) only by the action of the fluid. The dispenser (3) and the electrode (4) are arranged in a predetermined relative position which maintains constant over time the geometric shape of the volume of fluid present between them.

42 Claims, 3 Drawing Sheets ical current pass between a selected portion of skin and an electrode through a transport fluid interposed between the skin and the electrode and in which are dissolved or dispersed the molecules of the substance to be administered (usually in ionic, or electrolytic, or otherwise electrically charged form). The electrical circuit is closed applying one or more counter-electrodes on different parts of the skin from the treated one. The electrical current is applied according to an appropriate time-based wave form which allows to transfer the substances at a predetermined depth into the skin and based on predetermined mean square values over time.

DEVICE FOR THE TRANSCUTANEOUS ADMINISTRATION OF SUBSTANCES BY MEANS OF IONTOPHORESIS

BACKGROUND OF THE INVENTION

The invention relates to a device for the transcutaneous administration of substances by means of iontophoresis.

Transcutaneous iontophoresis is a known technique for administering substances to the body through the skin in localised fashion and with minimum haematic absorption of the substances, reducing the risk of side effects linked to their uncontrolled diffusion. Some substances which can be administered may be, by way of example, drugs, herbal remedies, cosmetic and homeopathic products. Transcutaneous iontophoresis is used, for instance, in aesthetic medicine (for instance in the treatment of cutaneous tissue blemishes) or in pain relieving, relaxing or tonicising therapies.

Transcutaneous iontophoresis consists of letting an electrical current pass between a selected portion of skin and an electrode through a transport fluid interposed between the skin and the electrode and in which are dissolved or dispersed the molecules of the substance to be administered (usually in ionic, or electrolytic, or otherwise electrically charged form). The electrical circuit is closed applying one or more counter-electrodes on different parts of the skin from the treated one. The electrical current is applied according to an appropriate time-based wave form which allows to transfer the substances at a predetermined depth into the skin and based on predetermined mean square values over time.

The transport fluid is usually in the form of a gel.

Appropriate devices are constructed to apply this technique.

In particular, known devices for the transcutaneous administration of substances by means of iontophoresis comprise a hollow operative head made of plastic material, provided with two openings on two opposite sides. An opening, into which is inserted a container of the fluid, acts as an inlet for the fluid. The other opening is closed to measure, except for a minimum space along the long edges, by a plastic roller, free to rotate about its own axis and acting as a dispenser of the transport fluid. The part of the roller inside the cavity is in contact with the fluid coming from the container and it rotates, by effect of friction with the skin, when the roller is applied to the skin with the device kept in motion. The roller thereby brings the part covered with fluid in contact with the skin, distributing the fluid. To continue dispensing the fluid, the roller must thus be maintained in continuous rotation. A thin lamina folded in the shape of an "L" is inserted into the chamber as an electrode. The short side of the lamina is fastened to the wall of the operative head and it bears an electrical terminal external to the head, connected with a voltage driven current generator (which, in turn, is connected to one or more counter-electrodes). The long side of the lamina faces the roller along the axis of rotation with a plane of lay converging on the axis itself and practically nearly in contact therewith. The electrode thus applies voltage at a very short distance from the surface of the roller and the current, to reach the skin, must travel through the whole circumference of a section of the roller within the very thin layer of fluid adhering to its surface. Given the characteristics of the fluid, the electrical impedance of this segment is usually high. Furthermore, it is highly variable and its value cannot be reliably controlled. The thickness of the fluid layer distributed on the cylinder in the outer part is variable over time according to the conditions of the skin, of the pressure exerted thereon by the roller, of the deformation of the operative head due to the pressure of the operator's fingers, which alters the geometry of the long sides of the aperture whereto the roller is applied. Moreover, when the skin is already moistened by the fluid, friction on the skin may not be sufficient to cause the roller to rotate (unless a strong pressure is exerted on the skin, which can be annoying for the patient). The roller thus dries up, stopping its distribution of fluid, and the electrical impedance imposed on the generator increases. Additionally, the lamina, which is fastened only on one side and very thin, can tend to deform elastically. The device is voltage driven and it maintains a given current (according to a certain waveform). Therefore, impedance variations may give rise to voltage fluctuations and peaks which can cause discomfort and even small burns to the patient. Moreover, the plastic roller is easily scratched and deteriorates, diminishing its ability to rotate and drive the fluid and becoming difficult to clean. In addition, it cannot be easily sterilised.

SUMMARY OF THE INVENTION

An object of the present invention is to overcome the aforementioned drawbacks, making available a device for the transcutaneous administration of substances by means of iontophoresis which imposes to the generator a constant and predetermined value of impedance. Another object of the present invention is to make available a device for the transcutaneous administration of substances by means of iontophoresis which imposes to the generator a value of impedance that is easily regulated according to treatment type and transport fluid.

These and other objects, which will become more readily apparent in the description that follows, are achieved, in accordance with the present invention, by a device for the transcutaneous administration of substances by means of iontophoresis having structural and functional characteristics in accordance with the appended independent claims, additional embodiments of said device being identified in the appended and corresponding dependent claims.

BRIEF DESCRIPTION OF THE DRAWINGS

The invention is described in greater detail hereafter with the aid of the drawings, which represent an embodiment provided purely by way of non limiting example.

DESCRIPTION OF THE PREFERRED EMBODIMENTS

Figure 1:
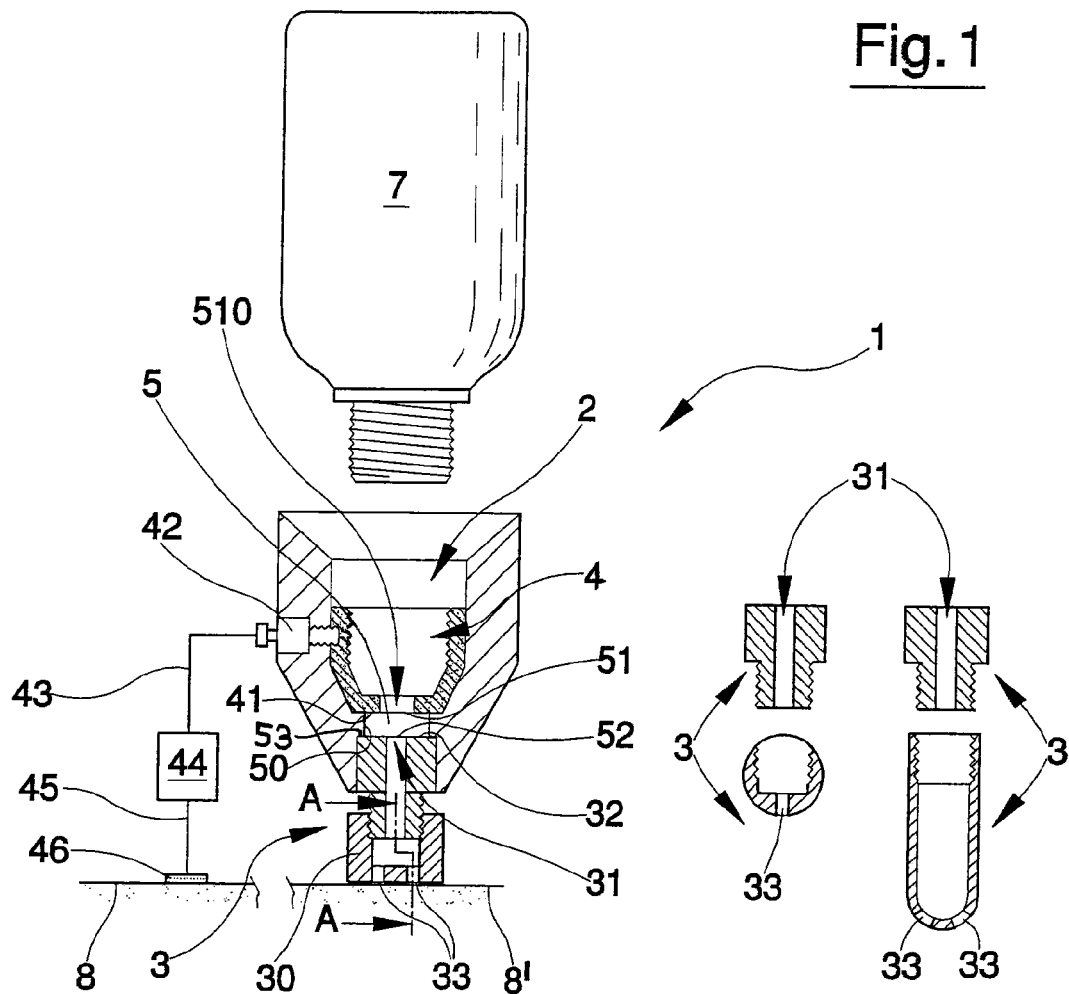
FIG. 1 shows a partially sectioned side view of a device according to the invention with two details of as many variants of the dispenser (partially sectioned along the trace A-A).

In the present context and unless otherwise expressly stated, the term "cylinder" generally means the solid enclosed by the straight lines (called "generatrices") conducted mutually parallel by the points of a closed line (called "directrix") whose shape may also be different from circular and, at the limit, even polygonal (in which case the "cylinder" would be identified with a prism). If the bases or ends of the cylinder are perpendicular to the generatrices, the cylinder is called "straight".

With reference to the figures, a device for the transcutaneous administration of substances by means of iontophoresis comprises an operative head 1 provided with an inlet 2 for a fluid transporting substances to be administered, with a fluid dispenser 3 which has a part 30 in contact with the skin, with an electrode 4 positioned on a path of the fluid from the inlet 2 to the dispenser 3. In general, the inlet 2 can be connected in various manners to a source or tank of fluid and the operative head 1 can be directly hand held to operate on the patient. Conveniently, as in prior art solutions, the device may comprise a container 7 of the fluid coupled with the inlet 2 in various manners. It may be fixed (and, in this case, the container 7 must be refillable or, at least, be a housing of a replaceable fluid cartridge) or removable (for example, as in FIG. 1, by means of a threaded coupling).

Generally, the operative head 1 has a main body made of insulating material which, as shown in the figures, may have a first straight cylindrical part with circular cross section and a second cone frustum shaped or slightly tapered part to facilitate its handling. In regards to the characteristics of the transport fluid and of the substances to be administered, what has been stated above applies. The fluid is preferably a gel. The substances can also be dissolved into it in electrolytic form.

Obviously, as provided by iontophoresis technique, the electrode 4 is generally in contact with the external terminal 42, connected with a voltage driven current generator 44 by means of a first conductor cable 43. The generator 44 is in turn connected, by means of at least a second conductor cable 45, to at least a counter electrode 46 positioned on a first portion of skin 8, to close the circuit.

In the device according to the invention, characteristically the dispenser 3 is made of electrically conducting material and is in electrical contact with the electrode 4 only by the action of the fluid. Moreover, in combination, the dispenser 3 and the electrode 4 are arranged in a predetermined relative position which maintains constant over time the geometric shape of the volume of fluid present between them.

Therefore, the potential of a second portion of skin 8', whereon the contact part 30 acts, is carried by the metallic body of the dispenser 3 (minus the minimal voltage drop which takes place in the very thin layer of fluid on the skin) to the border of the geometric shape of the volume of fluid present between the dispenser 3 and the electrode 4, which remains constant over time. Only in said volume of fluid does current flow from the electrode 4 to the dispenser 3 and hence the difference in potential between the electrode 4 and the second portion of skin 8' is substantially given by the path of the current in said volume and, since the fluid is homogeneous and isotropic, the impedance seen by the generator always remains substantially constant once the geometry of the volume is defined. Obviously, the material whereof the body of the operative head 1 is made must be rigid or the thickness of the walls of the body of the operative head 1 must be sufficient to inhibit their deformation. A similar condition applies to the electrode 4 and to the dispenser 3. The dispenser 3, being rigid and made of a material which can also be a metal, could also be a rotating element (as in the prior art), for instance a sphere caged in a guide. Highly preferably, however, in the present invention, as shown in the figures, the dispenser 3 is fixed relative to the operative head 1, it has at least an inlet 31 for the inflow of the fluid into it and on its part 30 in contact with the skin it has at least a hole 33 for the outflow of the fluid towards the skin connected with the inlet 31. In this way, even if, for various reasons, no fluid should be present on the surface of the contact part 30, the hole 33 would always bring a part of the fluid (contained in the operative head 1) in contact with the skin, thus maintaining substantially unaltered the impedance characteristics seen by the generator 44. Advantageously, the dispenser 3 is made of stainless steel. In addition to being a good conductor of electricity, it can thus be easily cleaned and sterilised and does not deteriorate easily.

Conveniently, in the operative head 1 is obtained along the path of the fluid a segment 5 of predetermined length, which separates the electrode 4 from the dispenser 3, has electrically insulating lateral walls 50, has a first end 51 defined by a surface portion 41 of the electrode 4 and having at least a passage 510 for the fluid, has a second end 52 defined by a surface portion 32 of the dispenser 3. The geometry of the volume of fluid present between the electrode 4 and the dispenser 3 is thereby defined in an exact and simple manner. In this case, when the dispenser 3 is fixed relative to the operative head 1 and has at least the inlet 31 for the entrance of the fluid in its interior and, on its part 30 in contact with the skin, it has at least the hole 33 for the outflow of the fluid towards the skin connected with the inlet 31, the inlet 31 is obtained in the second end 52 of the segment 5 of the path of the fluid.

Preferably, the surface portion 41 of the electrode 4 and the surface portion 32 of the dispenser 3 are plane.

Advantageously, moreover, as shown in FIG. 1, the segment 5 is straight cylindrical with predetermined section and the first and the second end 51, 52 are its bases. Said ends may be circular. The geometry of the segment 5 is thus particularly simple.

In general, advantageously the device may comprise means for regulating the relative position of the dispenser 3 and of the electrode 4, to vary or control in predetermined fashion the impedance imposed on the generator 44 according to the type of fluid or of electrolyte and/or of substance to be administered, or according to the type of treatment and/or of skin. In particular, the device comprises means for adjusting the distance between the planar surface portion 32 of the dispenser 3 and the planar surface portion 41 of the electrode 4. Said means can be of various kinds. Preferably, they may provide for adjustment with micrometre screw acting either on the dispenser 3 or on the electrode 4 (or on parts thereof) in such a way as to make them slide in guided fashion along the axis of the segment 5. In a preferred embodiment of the invention shown in FIG. 1, the dispenser 3 is at least partially inserted in a cylindrical conduit whose lateral surface defines the lateral walls 50 of the straight cylindrical segment 5 of the fluid path. The position adjustment means can thus be applied in very simple fashion, using the cylindrical conduit directly as a guide (in this case, the cylindrical conduit being straight and, preferably, with circular cross section).

The definition of the value of the surface area of the section of the cylindrical segment 5 can also be used to set the impedance value.

Figure 3:
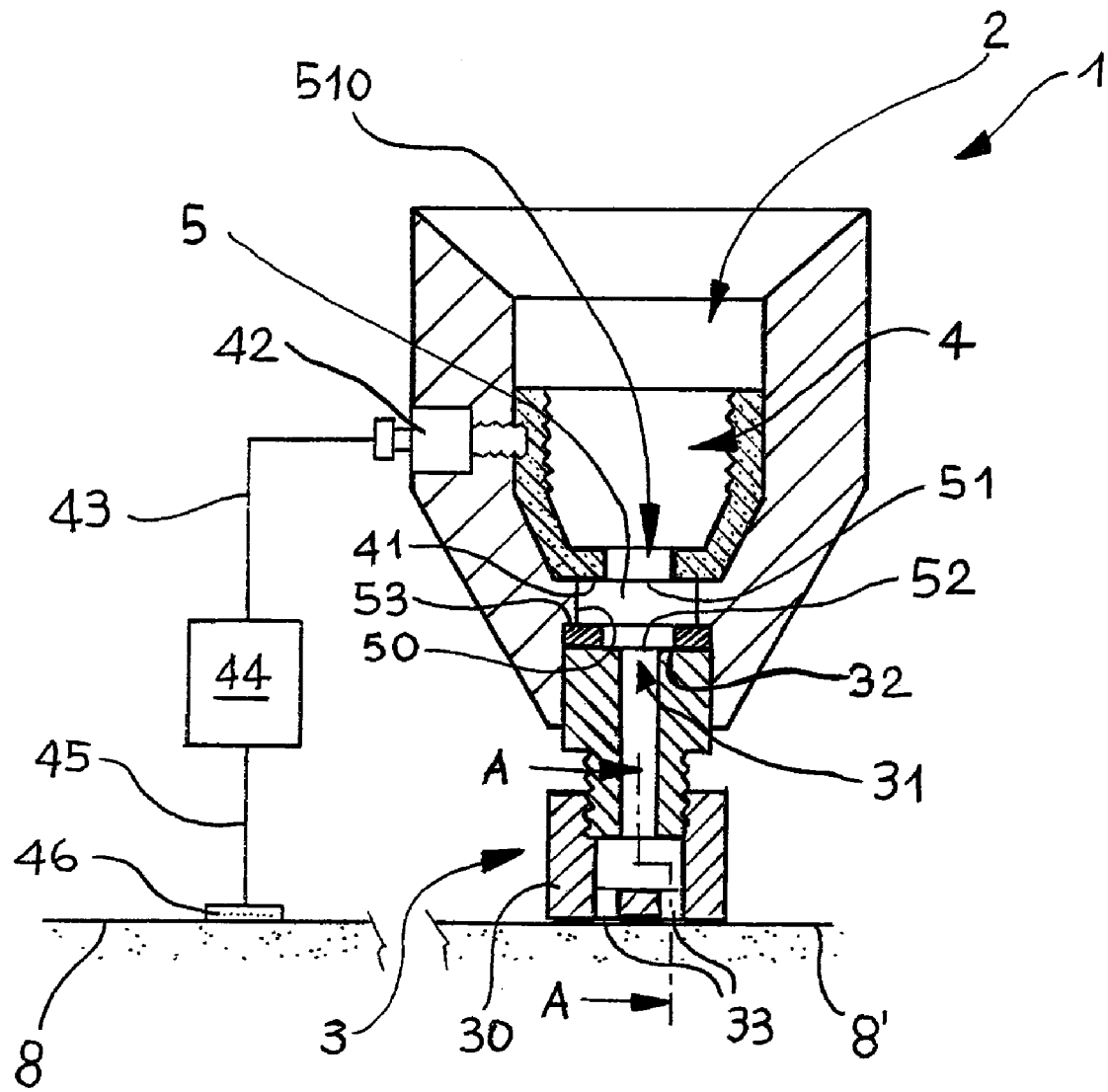
FIG. 3 shows a detail of the device illustrated in FIG. 1, with evidence of an embodiment of the means for adjusting the relative position of the dispenser and of the electrode.
Figure 4:
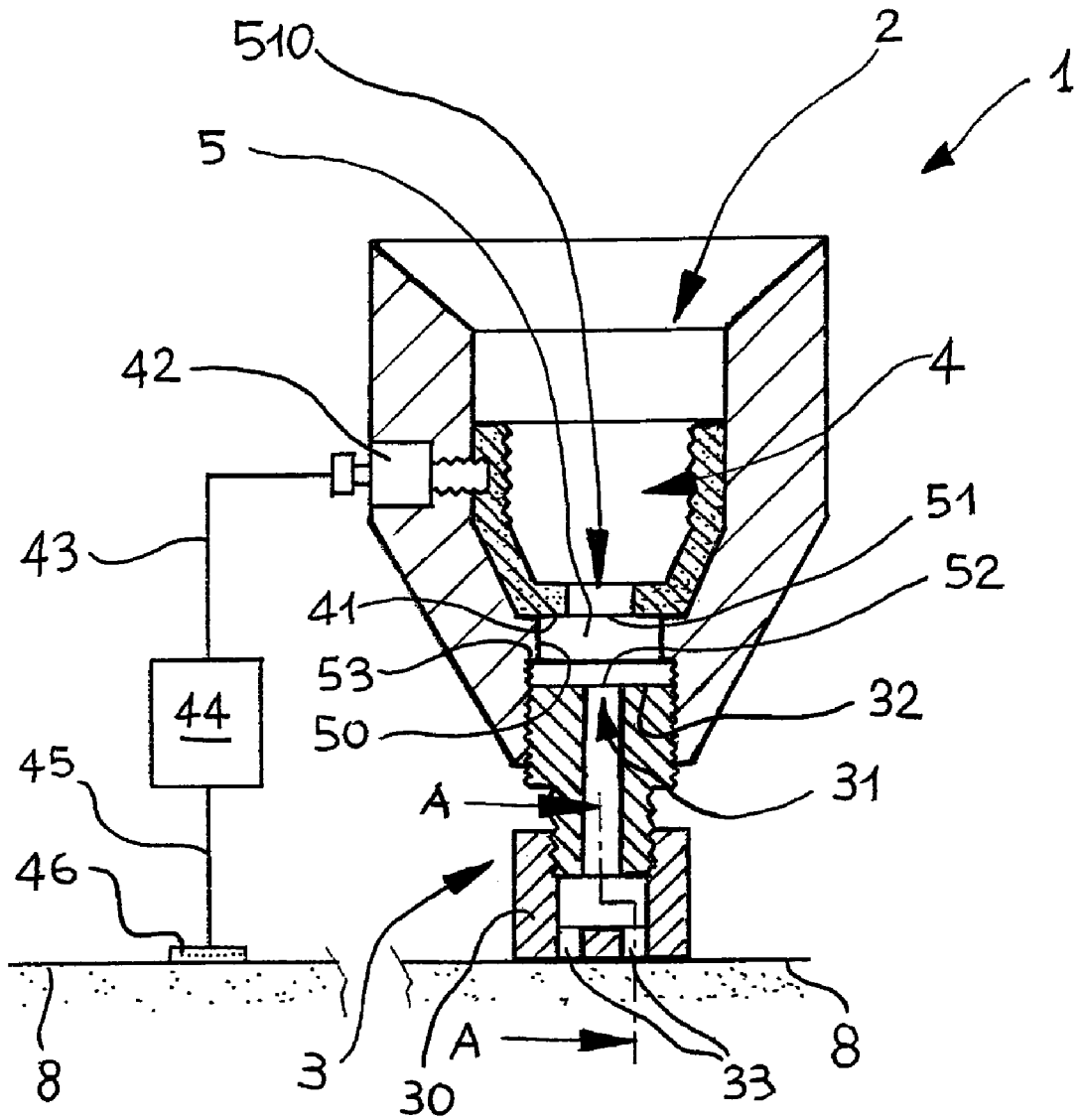
FIG. 4 shows a detail of the device illustrated in FIG. 1, with evidence of a further embodiment of the means for adjusting the relative position of the dispenser and of the electrode.

Advantageously, along the cylindrical conduit is obtained a small abutment 53 for arresting the insertion of the dispenser 3 into the conduit, which defines a minimum value of the length of the straight cylindrical segment 5. As illustrated in FIG. 3, by inserting diaphragms it is possible to modify the position of the abutment and, hence, the minimum length of the segment 5 (in the absence of micrometre adjustments, this can also be a coarse system for varying or controlling impedance).

Figure 2:
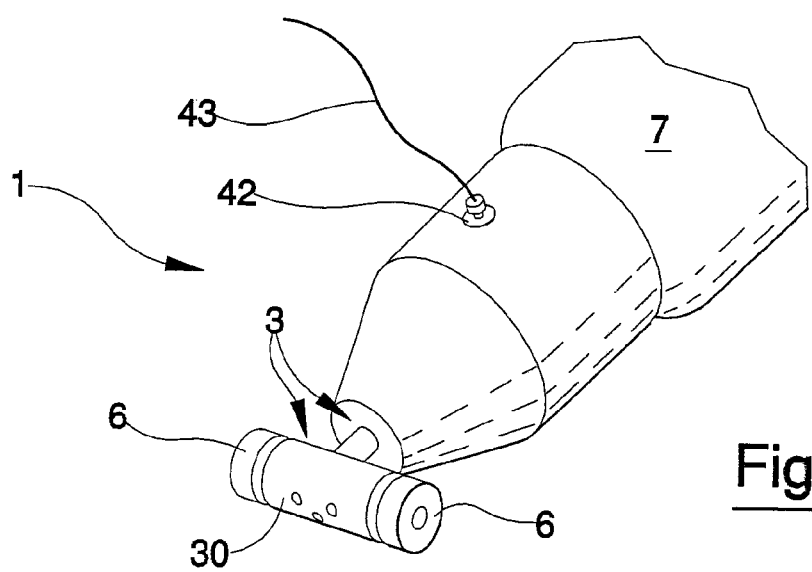
FIG. 2 shows a schematic perspective view of an embodiment of the device with detail of the operative head.

Moreover, advantageously, as shown in FIG. 1, in the part 30 of the dispenser 3 in contact with the skin are obtained at least two holes 33 in predetermined position. In the part 30 of the dispenser 3 in contact with the skin can also be obtained a plurality of holes 33 distributed according to a predetermined pattern, as shown in FIG. 2. As FIG. 1 clearly shows, where three examples of dispenser 3 are shown (one is shown in the operative head 1 and two are shown separately), very advantageously the part 30 in contact with the skin is removable. This allows either to clean it and/or sterilise it separately or to replace it with another one, contoured and shaped differently for a different use. In particular, in addition to a simple cylindrical shape (as shown in FIG. 2, and possibly with ample axial dimension in order simultaneously to treat an ample area of skin), the part 30 in contact with the skin can have a special contour which allows it to reach small or hidden parts of skin. In particular, the part 30 in contact with the skin is elongated and has reduced cross section (for instance in the form of a long "nose"). The association between the part 30 in contact with the skin and the remaining part of the dispenser 3 can, for instance, be achieved with a threaded coupling (as shown in FIG. 1) or with another type of coupling. As also shown in FIG. 1, the portion 30 in contact with the skin can be hollow or, otherwise, comprise a compensation compartment downstream of a segment of connecting conduit between the inlet 31 and the contact part 30 itself, into which is collected a certain quantity of fluid which can assure a continuous and constant dispensing of fluid from the hole or holes 33. As shown in FIG. 2, the device can comprise rolling friction means 6 to facilitate the motion on the skin of the part 30 in contact with the skin. However, this additional characteristic is not necessary: if the steel whereof the portion 30 in contact with the skin is made is well polished, the presence of even a very small quantity of fluid is sufficient to assure its ability to slide.

In the particular embodiment specifically illustrated in FIG. 1, the electrode 4 is in the form of a bushing (for instance also made of stainless steel), inserted coaxially to the body of the operative head 1 in a related seat and frontally bearing a planar part which constitutes the surface portion 41 of the electrode 4. The interior of the bushing can easily be threaded. This form of electrode, particularly simple, rigid and solid, is particularly suitable for the objects of the invention.

As is readily apparent from the description, the invention achieves important advantages.

First of all, problems to the patient, due to impedance variability, are prevented.

Secondly, load impedance can be adjusted accurately according to the characteristics of the fluid, to the type of treatment or of skin.

An additional, important advantage is that the device can easily be adapted to all requirements or skin areas.

Moreover, a no less important advantage consists of the ability to clean and sterilise the operative head with ease, or just the part 30 of the dispenser 3 in contact with the skin.

The invention thus conceived can be subject to numerous modifications and variations, without thereby departing from the scope of the inventive concept that characterises it.

Moreover, all components can be replaced with other, technically equivalent elements.

In practice all materials employed, as well as the dimensions, may be any, depending on requirements.

What is claimed:

1. Device for the transcutaneous administration of substances by means of iontophoresis, comprising an operative head provided with an inlet for a fluid transporting substances to be administered, with a fluid dispenser which has a part in contact with the skin, with an electrode located in a main body of the operative head, the electrode being positioned on a path of the fluid from the inlet to the dispenser, wherein: the dispenser is made of electrically conducting material and is in electrical contact with the electrode only by the action of the fluid; the dispenser and the electrode are arranged in a predetermined relative position which maintains constant over time the geometric shape of the volume of fluid present between them; the electrode being connected to a voltage driven current generator which, in turn, is connected to at least a counter electrode positioned on a first portion of skin, to close the circuit, the part of the dispenser in contact with the skin acting on a second portion of skin.

2. A device as claimed in claim 1, wherein it comprises means for adjusting the relative position of the dispenser and of the electrode.

3. A device as claimed in claim 1, wherein in the operative head is obtained along the path of the fluid a segment of predetermined length, which separates the electrode from the dispenser, by providing electrically insulating lateral walls between a surface portion of the electrode and a surface portion of the dispenser; the surface portion of the electrode defining a first end of the segment and having at least a passage for the fluid, the surface portion of the dispenser defining a second end of the segment.

4. A device as claimed in claim 2, wherein in the operative head is obtained along the path of the fluid a segment of predetermined length, which separates the electrode from the dispenser, by providing electrically insulating lateral walls between a surface portion of the electrode and a surface portion of the dispenser; the surface portion of the electrode defining a first end of the segment having at least a passage for the fluid, the surface portion of the dispenser defining a second end of the segment.

5. A device as claimed in claim 3, wherein the surface portion of the electrode and the surface portion of the dispenser are planar and said segment is straight cylindrical with predetermined cross section and the first and the second end are its bases.

6. A device as claimed in claim 4, wherein the surface portion of the electrode and the surface portion of the dispenser are planar and said segment is straight cylindrical with predetermined cross section and the first and the second end are its bases.

7. A device as claimed in claim 5, wherein the dispenser is at least partially inserted in a cylindrical conduit whose lateral surface defines the lateral walls of the straight cylindrical segment of the path of the fluid.

8. A device as claimed in claim 6, wherein the dispenser is at least partially inserted in a cylindrical conduit whose lateral surface defines the lateral walls of the straight cylindrical segment of the path of the fluid.

9. A device as claimed in claim 7, wherein along the conduit is obtained an abutment for arresting the insertion of the dispenser into the conduit, which defines a minimum value of the length of the straight cylindrical segment.

10. A device as claimed in claim 8, wherein along the conduit is obtained an abutment for arresting the insertion of the dispenser into the conduit, which defines a minimum value of the length of the straight cylindrical segment.

11. A device as claimed in claim 1, wherein the dispenser is fixed relative to the operative head, has at least an inlet for the entrance of the fluid in its interior and on its part in contact with the skin it has at least a hole for the outflow of the fluid towards the skin, connected with the inlet.

12. A device as claimed in claim 2, wherein the dispenser is fixed relative to the operative head, has at least an inlet for the entrance of the fluid in its interior and on its part in contact with the skin it has at least a hole for the outflow of the fluid towards the skin, connected with the inlet.

13. A device as claimed in claim 3, wherein the dispenser is fixed relative to the operative head, has at least an inlet for the inflow of the fluid in its interior and on its part in contact with the skin it has at least a hole for the outflow of the fluid towards the skin connected with the inlet, the inlet being obtained in the second end of the segment of the path of the fluid.

14. A device as claimed in claim 4, wherein the dispenser is fixed relative to the operative head, has at least an inlet for the inflow of the fluid in its interior and on its part in contact with the skin it has at least a hole for the outflow of the fluid towards the skin connected with the inlet, the inlet being obtained in the second end of the segment of the path of the fluid.

15. A device as claimed in claim 11, wherein the part in contact with the skin is removable.

16. A device as claimed in claim 12, wherein the part in contact with the skin is removable.

17. A device as claimed in claim 13, wherein the part in contact with the skin is removable.

18. A device as claimed in claim 14, wherein the part in contact with the skin is removable.

19. A device as claimed in claim 11, wherein it comprises rolling friction means to facilitate the motion on the skin of the part in contact with the skin.

20. A device as claimed in claim 12, wherein it comprises rolling friction means to facilitate the motion on the skin of the part in contact with the skin.

21. A device as claimed in claim 13, wherein it comprises rolling friction means to facilitate the motion on the skin of the part in contact with the skin.

22. A device as claimed in claim 14, wherein it comprises rolling friction means to facilitate the motion on the skin of the part in contact with the skin.

23. A device as claimed in claim 15, wherein it comprises rolling friction means to facilitate the motion on the skin of the part in contact with the skin.

24. A device as claimed in claim 16, wherein it comprises rolling friction means to facilitate the motion on the skin of the part in contact with the skin.

25. A device as claimed in claim 17, wherein it comprises rolling friction means to facilitate the motion on the skin of the part in contact with the skin.

26. A device as claimed in claim 18, wherein it comprises rolling friction means to facilitate the motion on the skin of the part in contact with the skin.

27. A device as claimed in claim 1, wherein it comprises a container of the fluid coupled to the inlet.

28. A device as claimed in claim 2, wherein it comprises a container of the fluid coupled to the inlet.

29. A device as claimed in claim 3, wherein it comprises a container of the fluid coupled to the inlet.

30. A device as claimed in claim 4, wherein it comprises a container of the fluid coupled to the inlet.

31. A device as claimed in claim 11, wherein it comprises a container of the fluid coupled to the inlet.

32. A device as claimed in claim 12, wherein it comprises a container of the fluid coupled to the inlet.

33. A device as claimed in claim 13, wherein it comprises a container of the fluid coupled to the inlet.

34. A device as claimed in claim 14, wherein it comprises a container of the fluid coupled to the inlet.

35. A device as claimed in claim 15, wherein it comprises a container of the fluid coupled to the inlet.

36. A device as claimed in claim 16, wherein it comprises a container of the fluid coupled to the inlet.

37. A device as claimed in claim 17, wherein it comprises a container of the fluid coupled to the inlet.

38. A device as claimed in claim 18, wherein it comprises a container of the fluid coupled to the inlet.

39. A device as claimed in claim 19, wherein it comprises a container of the fluid coupled to the inlet.

40. A device as claimed in claim 20, wherein it comprises a container of the fluid coupled to the inlet.

41. A device as claimed in claim 21, wherein it comprises a container of the fluid coupled to the inlet.

42. A device as claimed in claim 22, wherein it comprises a container of the fluid coupled to the inlet.

* * * * *